United States Patent [19]

Schumacher et al.

[11] Patent Number: 4,990,453

[45] Date of Patent: Feb. 5, 1991

[54] MODIFIED PSEUDOMONAS PUTIDA CREATINE AMIDINOHYDROLASE

[75] Inventors: Günther Schumacher; Peter Buckel, both of Bernried, Fed. Rep. of Germany

[73] Assignee: Boehringer Mannheim GmbH, Mannheim, Fed. Rep. of Germany

[21] Appl. No.: 192,485

[22] Filed: May 11, 1988

[30] Foreign Application Priority Data

May 12, 1987 [DE] Fed. Rep. of Germany ....... 3715841
Feb. 3, 1988 [DE] Fed. Rep. of Germany ....... 3803175

[51] Int. Cl.$^5$ .................. C12N 15/00; C12N 9/36; C12N 9/96; C12N 9/99
[52] U.S. Cl. .................. 435/231; 435/172.3; 435/252.34; 435/69.1; 435/877; 435/320.1; 935/14; 935/82; 935/10
[58] Field of Search .................. 435/227, 228, 70, 68, 435/320, 172.3, 18, 231, 252, 849, 877, 231, 252.34; 530/350; 935/14, 82, 10

[56] References Cited

U.S. PATENT DOCUMENTS

| | | | |
|---|---|---|---|
| 3,912,588 | 10/1975 | Mollering | 195/29 |
| 4,039,384 | 8/1977 | Suzuici | 195/62 |
| 4,692,409 | 9/1987 | Kisumi | 435/109 |
| 4,861,717 | 8/1989 | Schumacher | 435/172.3 |

FOREIGN PATENT DOCUMENTS

| | | |
|---|---|---|
| 0187138 | 7/1986 | European Pat. Off. . |
| 3500184 | 8/1986 | Fed. Rep. of Germany . |
| 3707172 | 9/1987 | Fed. Rep. of Germany . |

OTHER PUBLICATIONS

Patent Abstracts of Japan 6: 106 (C–108) (984) 6/16/82.
Bryan et al., Proteins: Structure, Function & Genetics 1(4): 326–334 (1986).

*Primary Examiner*—Robin L. Teskin
*Assistant Examiner*—Michelle S. Marks
*Attorney, Agent, or Firm*—Felfe & Lynch

[57] ABSTRACT

A stable mutant form of creatine amidohydrolase is disclosed. This enzyme is formed via expression of altered DNA, which may be in plasmid form. Also disclosed is a method for determining creatinine using the mutant form.

2 Claims, 2 Drawing Sheets

FIG. 1.

```
         10                  30                  50
ATGCAAATGCCCAAGACGCTCCGCATCCGTAACGGCGACAAGGTTCGCTCCACCTTCTCC
MetGlnMetProLysThrLeuArgIleArgAsnGlyAspLysValArgSerThrPheSer 70                  90                 110
GCCCAGGAATACGCCAATCGCCAAGCCAGGCTGCGCGCCCACCTGGCGGCGGAGAACATC
AlaGlnGluTyrAlaAsnArgGlnAlaArgLeuArgAlaHisLeuAlaAlaGluAsnIle 130                 150                 170
GACGCCGCGATCTTCACCTCGTACCACAACATCAACTACTACTCCGACTTCCTCTACTGC
AspAlaAlaIlePheThrSerTyrHisAsnIleAsnTyrTyrSerAspPheLeuTyrCys 190                 210                 230
TCCTTCGGCCGCCCCTACGCGTTGGTGGTGACCCAGGACGACGTCATCAGCATCAGCGCC
SerPheGlyArgProTyrAlaLeuValValThrGlnAspAspValIleSerIleSerAla 250                 270                 290
AACATCGACGGCGGCCAGCCGTGGCGCCGCACCGTCGGCACCGACAACATCGTCTACACC
AsnIleAspGlyGlyGlnProTrpArgArgThrValGlyThrAspAsnIleValTyrThr 310                 330                 350
GACTGGCAGCGCGATAACTACTTCGTCGCCATCCAGCAGGCGTTGCCGAAGGCCCGCCGC
AspTrpGlnArgAspAsnTyrPheValAlaIleGlnGlnAlaLeuProLysAlaArgArg 370                 390                 410
ATCGGCATCGAACATGACCACCTGAACCTGCAGAACCGCGACAAGCTGGCCGCGCGCTAT
IleGlyIleGluHisAspHisLeuAsnLeuGlnAsnArgAspLysLeuAlaAlaArgTyr 430                 450                 470
CCGGACGCCGAGCTGGTGGACGTGGCCGCCGCCTGCATGCGTATGCGCATGATCAAATCC
ProAspAlaGluLeuValAspValAlaAlaAlaCysMetArgMetArgMetIleLysSer 490                 510                 530
GCCGAAGAGCACGTGATGATCCGCCACGGCGCGCGCATCGCCGACATCGGTGGTGCGGCG
AlaGluGluHisValMetIleArgHisGlyAlaArgIleAlaAspIleGlyGlyAlaAla 550                 570                 590
GTGGTCGAAGCCCTGGGCGACCAGGTACCGGAATACGAAGTGGCGCTGCATGCCACCCAG
ValValGluAlaLeuGlyAspGlnValProGluTyrGluValAlaLeuHisAlaThrGln 610                 630                 650
GCCATGGTCCGCGCCATTGCCGATACCTTCGAGGACGTGGAGCTGATGGATACCTGGACC
AlaMetValArgAlaIleAlaAspThrPheGluAspValGluLeuMetAspThrTrpThr
```

FIG. 1. (cont.)

```
          670                690                710
TGGTTCCAGTCCGGCATCAACACCGACGGCGCGCACAACCCGGTGACCACCCGCAAGGTG
TrpPheGlnSerGlyIleAsnThrAspGlyAlaHisAsnProValThrThrArgLysVal 730                750                770
AACAAGGGCGACATCCTCAGCCTCAACTGCTTCCCGATGATCGCCGGCTACTACACCGCG
AsnLysGlyAspIleLeuSerLeuAsnCysPheProMetIleAlaGlyTyrTyrThrAla 790                810                830
TTGGAGCGCACCCTGTTCCTCGACCACTGCTCGGACGACCACCTGCGTCTGTGGCAGGTC
LeuGluArgThrLeuPheLeuAspHisCysSerAspAspHisLeuArgLeuTrpGlnVal 850                870                890
AACGTCGAGGTGCATGAAGCCGGCCTGAAGCTGATCAAGCCCGGTGCGCGTTGCAGCGAT
AsnValGluValHisGluAlaGlyLeuLysLeuIleLysProGlyAlaArgCysSerAsp 910                930                950
ATCGCCCGCGAGCTGAACGAGATCTTCCTCAAGCACGACGTGCTGCAGTACCGCACCTTC
IleAlaArgGluLeuAsnGluIlePheLeuLysHisAspValLeuGlnTyrArgThrPhe 970                990                1010
GGCTACGGCCACTCCTTCGGCACGCTCAGCCACTACTACGGCCGCGAGGCCGGGTTGGAA
GlyTyrGlyHisSerPheGlyThrLeuSerHisTyrTyrGlyArgGluAlaGlyLeuGlu 1030               1050               1070
CTGCGCGAGGACATCGACACCGTGCTGGAGCCGGGCATGGTGGTGTCGATGGAGCCGATG
LeuArgGluAspIleAspThrValLeuGluProGlyMetValValSerMetGluProMet 1090               1110               1130
ATCATGCTGCCGGAAGGCCTGCCGGGCGCCGGTGGCTATCGCGAGCACGACATCCTGATC
IleMetLeuProGluGlyLeuProGlyAlaGlyGlyTyrArgGluHisAspIleLeuIle 1150               1170               1190
GTCAACGAGAACGGTGCCGAGAACATCACCAAGTTCCCCTACGGCCCGGAGAAAAACATC
ValAsnGluAsnGlyAlaGluAsnIleThrLysPheProTyrGlyProGluLysAsnIle

1210
ATCCGCAAATGA
IleArgLysEnd
```

MODIFIED PSEUDOMONAS PUTIDA CREATINE AMIDINOHYDROLASE

BACKGROUND OF THE INVENTION

The present invention is concerned with mutant forms of creatine amidinohydrolase which are more stable than the wild type enzyme and are, therefore, more suitable for the enzymatic determination of the creatinine content of a body fluid, such as serum, plasma and urine.

The enzyme creatine amidinohydrolase (EC 3.5.3.3) is used industrially for the determination of creatinine. It is used, inter alia, in clinical analysis for the diagnosis of kidney diseases in which the creatinine content occurring in the serum and urine differ from those of the healthy organism. Micro-organisms are known, for example types of Pseudomonas, which, with induction by creatine, are able to produce creatine amidinohydrolase in sufficient amount so that work up is worthwhile; however the achievable yields and the costs of isolation of the enzyme are still limiting factors for the industrial use of the enzyme.

As is described in Federal Republic of Germany Patent Specification No. 35 00 184, it is possible to isolate from *Pseudomonas putida* the gene coding creatine amidinohydrolase and to introduce it, for example, into plasmid pBR 322. After transformation of a micro-organism of the genus *Escherichia coli* or *Pseudomonas putida* with the new plasmid, it is possible to obtain creatine amidinohydrolase constitutively therefrom. This genetechnological production of creatine amidinohydrolase is more effective and easier to carry out than via isolation of the enzyme from an induced micro-organism which does not contain a plasmid. However, this process has the disadvantage that the wild type enzyme obtained therefrom has only a limited detergent and thermal stability and thus is not optimally suitable for use in clinical test processes.

It is an object of the present invention to provide creatine amidinohydrolase mutants which do not display the described disadvantages of the prior art or do so only to a slight extent.

SUMMARY OF THE INVENTION

According to the present invention, this object is achieved by mutant forms of creatine amidinohydrolase which catalyze the reaction:

corresponding to the wild type enzeyme, wherein, in comparison with the wild type enzyme, at least one amino acid change has taken place in position 109. This change concerns the amino acid alanine which has been replaced by valine. The so mutated enzyme has a considerably better stability than the wild type enzyme.

Apart from this amino acid change, without impairment of the enzymatic activity, other mutations on the amino acid template can also be present and a still higher stability can then be achieved. In addition to the amino acid change in position 109, a preferred enzyme contains a further amino acid change.

The present invention also provides the plasmids pBT 109 and pBT 119. These contain the creatine amidinohydrolase genes of the wild type but, in both plasmids, on the DNA template which expresses the creatine amidino-hydrolase there is not only the amino acid change at position 109, and in pBT 119 there is, at position, namely, position 355, an exchange of Val by Meth by corresponding exchange of the triplet coding these amino acids in the wild type gene. By sequencing of pBT 119, it has been ascertained that at position 1063 of the sequence in the coding strand, a G is replaced by A (G→A) so that the triplet GTG of the wild type is changed into ATG. A preferred micro-organism of the genus *Escherichia coli* according to the present invention, *Escherichia coli*, DSM 5105, contains the plasmid pBT 109 and a further preferred micro-organism *Escherichia coli*, DSM 4106, contains, according to the present invention, the plasmid pBT 119. According to the present invention, further preferred micro-organisms are those of the genus *Escherichia coli* or *Pseudomonas putida* which constitutively express a creatine amidinohydrolase which contains the said mutations.

DETAILED DESCRIPTION OF PREFERRED EMBODIMENTS

The preparation of the mutated enzymes according to the present invention takes place in that, according to known gene-technological methods, recombinant DNA is brought to expression in an appropriate expression system which contains a creatine amidinohydrolase gene which essentially has the sequence of the wild type gene but contains, at least in position 326 of the natural gene, a T instead of the desoxyribonucleotide C. A gene is preferably expressed in which, furthermore, a base is exchanged in a further position. Especially preferably, in position 1063, A is present instead of G.

As recombinant DNA, there is preferably expressed one of the plasmids pBT 109, DSM 4108P or pBT 119, DSN 4107P. However, as recombinant DNA, there can also be used any recombinant DNA which contains the DNA sequence for the wild type enzyme described in Federal Republic of Germany Patent Specification No. 35 00 184, or an equivalent thereof, coding according to the genetic code for the same amino acid sequence in which, however, at position 326 of the natural gene, the desoxyribonucleotide T is present instead of C. In such a recombinant DNA, in addition there can be present a further base exchange which leads to a further amino acid mutation in the enzyme. In position 1063, G is thereby preferably exchanged for A.

The mutant gene is produced according to methods known to the man skilled in the art by synthesis or cutting out of the DNA piece to be removed, whereby restriction enzymes are used, or by loop formation with a hybridizing oligonucleotide connecting by hybridization the ends remaining at the cuts on both sides of the sequence to be removed.

As expression system, there is preferred a micro-organism of the genus *Escherichia coli* or *Pseudomonas putida*. Especially preferred are *Escherichia coli* ED 8654, DSM 2102, or *Pseudomonas putida*. DSM 2106. Further processes of production according to the present invention involve culturing the preferred micro-organisms *Echerichia coli*, DSM 4105 and *Escherichia coli*, DSM 4106.

The present invention is also concerned with the use of mutated creatine amidinohydrolases according to the present invention, which are more stable than the wild type enzyme, for the determination of the creatinine content in serum, plasma and urine.

Investigations of the cloned creatine amidinohydrolase described in Federal Republic of German Patent Specification No. 35 22 184 have shown that the enzyme catalyses the the reaction sequence:

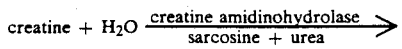

An increase of the rate of the substrate reaction cannot be achieved under the optimum working conditions by increasing the amount of enzyme. Under test conditions for the determination of the creatinine content of serum, plasma or urine at 37° C., the enzyme displays limited stability, which leads to a reduction of the substrate reaction at this temperature. The creatine amidinohydrolase according to the present invention which contains a mutation of the amino acid 109 of the wild type anzyme from alanine into valine, has, in comparison, under various test conditions e.g. (addition of detergent), a strongly increased detergent stability as compared to the same initial enzyme activity of the wild type enzyme, as is shown by the comparative experimental results set out in the following Table I. The temperature behavior under optimum conditions is shown in the following Table II.

activity, a still greater stability in comparison with the wild type enzyme (see Example 1, Table III).

With the creatine amidinohydrolase mutants according to the present invention, it is, therefore, possible to avoid enzyme activity loss in the case of the creatinine determination due to the detergent and thermal lability of the wild type enzyme and also to carry out such determinations dependably over longer periods of time than was hitherto possible. Because of the improved properties, a reduction of the amount of enzyme in the creatinine test is also possible.

The following Examples are given for the purpose of illustrating the present invention:

EXAMPLE 1

Cells of *Escherichia coli* DSM 4105, *Escherichia coli* DSM 4106 and, for comparison, *Escherichia coli* DSM 3143 (Federal Republic of Germany Patent Specification No. 35 00 184), were cultured overnight in 1 l. fermenters.

Medium rich medium (yeast extract 10 g/l/bacto tryptone 16

TABLE I

| | time (minutes) | creatine admidinohydrolase wild type (DE 35 00 184 Al) (DSM 3143) comparison | | | creatine amidinohydrolase mutant (amino acid 109 = Val) (DSM 4105) according to the invention | | | test conditions |
|---|---|---|---|---|---|---|---|---|
| I | 0 | 3.3 U/ml. (activity | = | 100%) | 3.0 U/ml. (activity | = | 100%) | Testmix 1 from test |
| | 15 | 1.9 U/ml. (residual activity | = | 59%) | 3.0 U/ml. (residual activity | = | 100%) | combination |
| | 30 | 0.6 U/ml. (residual activity | = | 18%) | 2.7 U/ml. (residual activity | = | 91%) | "Creatinin-PAP" |
| | 60 | 0.2 U/ml. (residual activity | = | 6%) | 2.5 U/ml. (residual activity | = | 83%) | (BM No. 839 434) |
| II | 0 | 3.3 U/ml. (activity | = | 100%) | 3.0 U/ml. (activity | = | 100%) | in 125 mmole/liter |
| | 15 | 0.7 U/ml. (residual activity | = | 21%) | 2.7 U/ml. (residual activity | = | 91%) | phosphate buffer + |
| | 30 | 0.0 U/ml. (residual activity | = | 0%) | 2.7 U/ml. (residual activity | = | 91%) | detergent |
| | 60 | 0.0 U/ml. (residual activity | = | 0%) | 2.1 U/ml. (residual activity | = | 71%) | |

The enzymes were incubated under the conditions given in the Table and subsequently an enzyme determination was carried out with the use of the test combination "urea" (BM Order No. 124770).

TABLE II

Enzyme determination under optimum conditions at different temperatures.
Test conditions: 20 mMole/liter phosphate buffer (pH 8.0).
1 = creatine amidinohydrolase wild type: 1.05 mg protein/ml (8.0 U/mg).
2 = creatine amidinohydrolase mutant: 1.10 mg protein/ml (8.7 U/mg) (amino acid 109 = Val).

| | creatinase residual activity in % (incubation in minutes) | | | | | |
|---|---|---|---|---|---|---|
| | 1. (DSM 3143) | | | 2. (DSM 4105) | | |
| temp. | 30 m. | 60 m. | 120 m. | 30 m. | 60 m. | 120 m. |
| 37° C. | 100 | 86 | 80 | 100 | 96 | 90 |
| 42° C. | 57 | 36 | 13 | 84 | 73 | 63 |
| 47° C. | 1 | 0.4 | 0 | 42 | 2 | 0 |
| 52° C. | 0 | — | — | 3 | — | — |

The enzyme were incubated under the given test conditions and subsequently an enzyme determination was carried out with the use of the test combination "urea" (BM Order No. 124 770).

The creatine amidinohydrolase enzyme according to the present invention which, in addition to this mutation, carries a further amino acid mutation, also possesses, in the case of almost the same initial enzyme g/l/NaCl
5 g/l)
0.4% glucose
100 mMole/liter phosphate buffer, pH 7.5.

After centrifuging for 15 minutes at 800 r.p.m., the cells were broken down in a French press and the creatine amidinohydrolase purified by fractionation over a molecular sieve (Sephacryl S 200).

The enzymes obtained were incubated under the conditions given in the following Table III and subsequently an enzyme determination was carried out with the use of the test combination "urea" (BM Order No. 124 770).

The following Table III gives the stability behavior of the creatine amidinohydrolase mutants according to the present invention in comparison with the wild type enzyme (Federal Republic of Germany Patent Specification No. 35 00 184—*Escherichia coli* DSM 3143).

TABLE III

Stability at 37° C.
Test conditions dissolved in a reaction mixture consisting of:
100 mmol/l phosphate buffer, pH 7.9
5 μmol/l potassium hexacynoferrate (II)
8.6 mmol/l 2,4,6-tribromo-3-hydroxybenzoic acid
0.25% detergent
5 mmol/l sodium cholate
0.8 mmol/l 4-aminophenazone 5 U/ml sarcosine oxidase
1 U/ml peroxidase
10 U/ml ascorbate oxidase
2 U/ml cholesterol esterase.

Incubation of creatine amidinohydrolase was as for the times indicated in the tables. The activity of creatine amidinohydrolase is determined as follows:

A $10^{-3}$ dilution is prepared from a solution containing 8.0 U/mg creatine amidinohydrolase wild type and 8.7 U/mg creatine amidinohydrolase mutant, respectively, and used for the test. In the case of less than 100% residual activity the solution is diluted less, e.g. $5 \times 10^{-2}$ or $10^{-2}$ times.

20 μl of this diluted solution are mixed with 100 ul phosphate buffer 12.5 mmol/l, pH 6.5, which contains 2.5 U/ml urease and 3.0 μl of 50 mM creatine in 0.01M phosphate buffer pH 7.6 and incubated for 10 minutes at 37° C. 500 μl of a solution of 0.106 mol/l phenol and 0.17 mmol/l sodium nitroprussiate as well as 500 μl of a solution consisting of 11 mmol/l sodium hypochlorite and 0.125N NaOH are added, mixed and incubated for 15 minutes at 37° C. Then the solution is passed into a cuvette and the extinction of the sample is measured at 550 nm against the reagent blank.

Initial activity: 12 U/ml (=100%)

| creatine amidinohydrolase from *Escherichia coli* (coding plasmid) | residual activity as % of the initial activity after | | | |
| --- | --- | --- | --- | --- |
| | 15 m. | 30 m. | 45 m. | 60 m. |
| DSM 3143 (pBT 2a-1, DSM 3148P) | 39 | 51 | 39 | 27 |
| DSM 4105 (pBT 109, DSM 4108P) | 96 | 90 | 84 | 84 |
| DSM 4106 (pBT 119, DSM 4107P) | 102 | 102 | 102 | 102 |

Comparison of the Michaelis constants (Km) at 37° C.
test conditions: 0.1 mole/liter Tris-HCl (pH 8.0)
(optimum test conditions)

| creatine amidinohydrolase from *Escherichia coli* (coding plasmid) | Km, mMole/liter |
| --- | --- |
| DSM 3143 (pBT 2a-1, DSM 3148P) | 25 |
| DSM 4105 (pBT 109, DSM 4108P) | 20 |
| DSM 4106 (pBT 119, DSM 4107P) | 16 |

EXAMPLE 2

The stable creatine amidinohydrolase mutant from the micro-organism *Escherichia coli* DSM 4105, which contains the plasmid pBT 109, was isolated from a 100 liter formation in the manner described in Federal Republic to Germany Patent Specification No. 35 00 184. 121 g of protein were obtained with a specific activity of 10.4 U/mg. This corresponds to a yield of 63%.

It will be understood that the specification and examples are illustrative but not limitative of the present invention and that other embodiments within the spirit and scope of the invention will suggest themselves to those skilled in the art.

We claim:

1. A modified *Pseudomonas putida* creatine amidinohydrolase characterized by having valine at amino acid position 109 and haivng enhanced stability in the presence of detergent and higher temperatures as compared to creatine amidinohydrolase not having valine at amino acid position 109.

2. The modified creatine amidinohydrolase of claim 1, comprising at least one further amino acid mutation.

* * * * *